Figure 1:
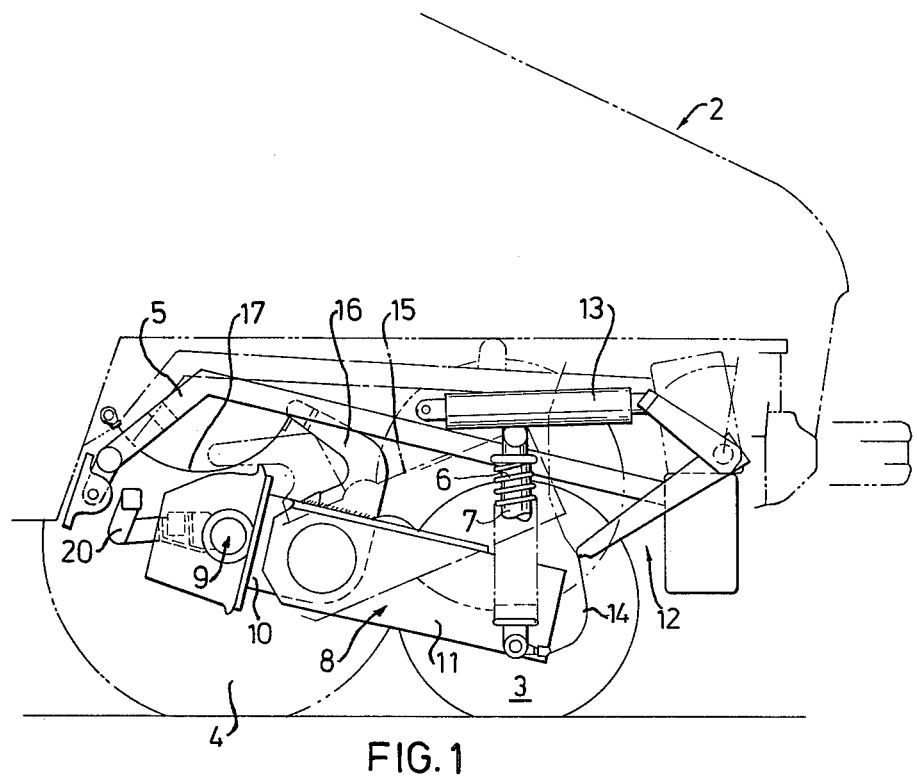

United States Patent [19]

Härdmärk et al.

[11] 4,098,111
[45] Jul. 4, 1978

[54] ROADWAY FRICTION MEASURING METHOD AND APPARATUS

[75] Inventors: Ragnar Malcus Härdmark; Bror Anders Sören Hanberger; Sven Edvin Forsberg, all of Linkoping, Sweden

[73] Assignee: Saab-Scania Aktiebolag, Sodertalje, Sweden

[21] Appl. No.: 763,081

[22] Filed: Jan. 27, 1977

[30] Foreign Application Priority Data

Mar. 31, 1976 [SE] Sweden .................................. 7603814

[51] Int. Cl.² ................................................ G01N 19/02
[52] U.S. Cl. ............................................. 73/9; 73/129
[58] Field of Search ...................... 73/9, 146, 128, 129

[56] References Cited

U.S. PATENT DOCUMENTS

| 2,496,405 | 2/1950 | Foufounis | 73/9 |
| 3,332,276 | 7/1967 | Clarke | 73/9 |
| 3,893,330 | 7/1975 | Shute et al. | 73/9 |
| 3,948,080 | 4/1976 | Boyd | 73/9 |

FOREIGN PATENT DOCUMENTS

| 1,015,251 | 9/1952 | France. |
| 1,476,730 | 3/1967 | France. |
| 1,924,584 | 6/1970 | Fed. Rep. of Germany. |

*Primary Examiner*—Jerry W. Myracle
*Attorney, Agent, or Firm*—Cushman, Darby & Cushman

[57] ABSTRACT

A method and apparatus for measuring and indicating limiting values for driving and braking vehicles in which a measuring wheel can be raised and lowered from a conventional wheeled vehicle to engage and disengage a substructure. The wheel is driven with a predetermined slip in relation to vehicle speed and the resulting loads detected by suitably mounted transducers. The signals produced by the transducers are combined in an electronic unit and displayed to indicate the braking force number, the coefficient of friction and resistance to rolling.

16 Claims, 4 Drawing Figures

ROADWAY FRICTION MEASURING METHOD AND APPARATUS

The present invention relates to a method and device in wheeled vehicles for measuring and indicating relevant limiting values for driving and braking the vehicle on a prevailing substructure, at least one measuring wheel incorporated in the wheeled vehicle being brought to engage, at least during a measured cycle, against the substructure and to move over the substructure with a predetermined slip applied to it in relation to the speed of the wheeled vehicle.

In measuring the coefficient of friction $\mu$ of a roadway, it is already known to equip a wheeled vehicle with a measuring wheel driven from a free-rolling wheel in the vehicle so that the measuring wheel is given a fixed slip determined by the intermediate transmission. Such wheeled measuring vehicles are made as trailers as a rule, and are preferably suited to measuring the coefficient of friction of roadways at low vehicle speeds. A trailer requires a very substantial towing vehicle and trailers tend to be unstable at high vehicle speeds. This means that a trailer-vehicle combination cannot be driven at the speeds which are relevant for aeroplanes during take-off and landing, since the varying wheel loadings brought about by its instability and unevenness in the substructure produce measuring results which are sufficiently accurate.

In calculating take-off and landing performance for aeroplanes, where the variable parameter in practice is the weight of the aeroplane, it is also desirable to correct for decreased braking effect on a substructure as a result of snow, slush and collection of water. Known measuring apparatuses are not capable of giving margins of safety on slippery runways, which correspond to the margins applying to dry summer runways. Other disadvantages are that the measuring staff must operate the measuring equipment from the outside of the prime-mover and that wear and roll resistance also occur on the measuring wheel while transporting the trailer.

One of the conditions enabling measurement of an optimum braking effect on a substructure to give a picture of the frictional qualities of a runway which are suitable for aeroplanes is that the measurement can be carried out in a satisfactory way at comparatively high vehicle speeds. The variation of the normal load acting on the measuring wheel at such speeds must be taken into account if the coefficient of friction is to be accurately measured.

With runways or highways on which there lie quantities of water, so-called aquaplanning occurs at high vehicle speeds. The aquaplanning phenomenon is caused by a film of water being formed between the tire and substructure, resulting in the friction between them assuming a low value, usually about 0.2. In practice, this means that the vehicle in question will be uncontrollable and that the risk of accidents is obvious. With aeroplanes it is of extremely great importance that the pilot is given information before landing about the speed at which aquaplanning can be expected to occur.

For aeroplanes landing on or taking off from a runway which is covered with snow or has quantities of water on it, it is also important that the pilot is given information about the roll resistance which the runway can be expected to give. Under such runway conditions, the roll resistance contributes substantially to braking the vehicle. As alternative information on the roll resistance a braking force number can be communicated to the aeroplane, this number expressing the total braking force in relation to the wheel load.

The purpose of the present invention is to provide a method and an apparatus for measuring road and/or runway properties to give vehicles moving at high speeds an optimum retardation on a prevailing substructure, at least one measuring wheel incorporated in a wheeled vehicle being brought to engage against the substructure, at least during the measuring cycle, and to move over it with a predetermined slip, the value of which is set in relation to the speed of the wheeled vehicle. According to the method of the present invention vertical and/or horizontal loads acting on the measuring wheel are continuously detected by at least one measuring transducer generating signals applied to an electronic unit for signal processing and resulting output signals from the electronic units are indicated in analogue and/or digital from on instruments or the like connected to the electronic unit.

Further a signal representing the momentary horizontal load on the measuring wheel is divided by a signal representing the momentary vertical load on the measuring wheel and the resulting output signal, representing the braking force number for the measuring wheel, is indicated in analogue and/or digital form on an instrument or the like.

To measure the coefficient of friction $\mu$ of the substructure the torque acting on the measuring wheel is detected by at least one measuring transducer generating signals corresponding thereto. Signals representing torque are applied to the electronic unit simultaneously with input signals representing vertical loads acting on the measuring wheel, said signals being applied to a dividing circuit in the electronic unit, in which a signal representing the momentary torque on the measuring wheel is divided by a signal representing the momentary vertical load on it. The resultant signal from the electronic unit, representing the coefficient of friction of the substructure is indicated in analogue and/or digital form on a conventional display or the like.

The difference between the horizontal load on the measuring wheel and the frictional force on it is also detected in the electronic unit, and a dependent signal representing the roll resistance of the measuring wheel is indicated in analogue and/or digital form on an instrument intended for this purpose.

The apparatus according to the invention, for carrying out the abovementioned method, comprises a raisable and lowerable, rotatably mounted measuring wheel which is in torque transmitting communication at a predetermined reduction with at least one of the ordinary wheels of the wheeled vehicle. At the measuring wheel a measuring transducer is mounted for detecting vertical and/or horizontal loads acting on the measuring wheel.

Figure 3:
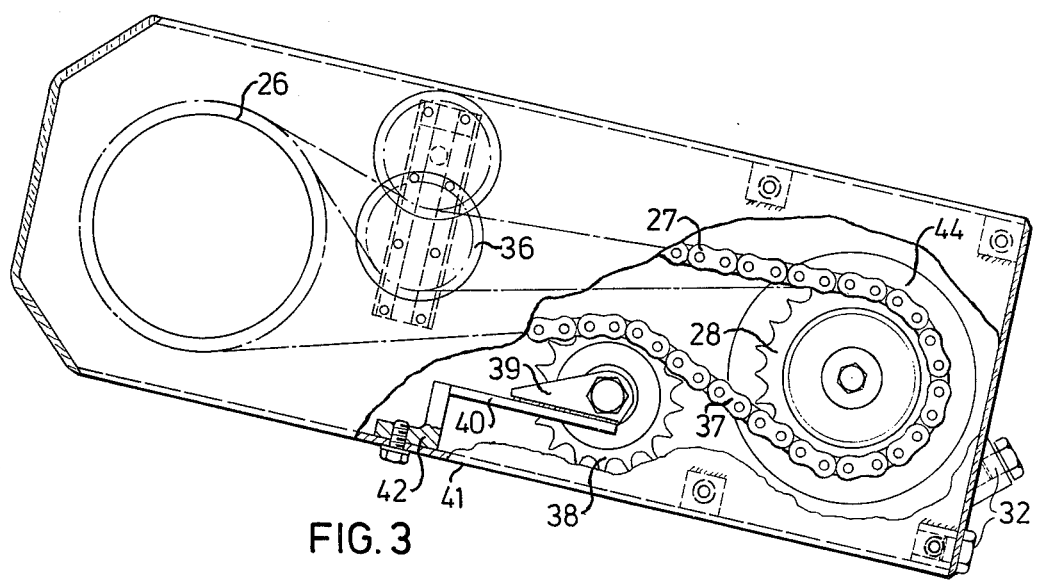
Figure 4:
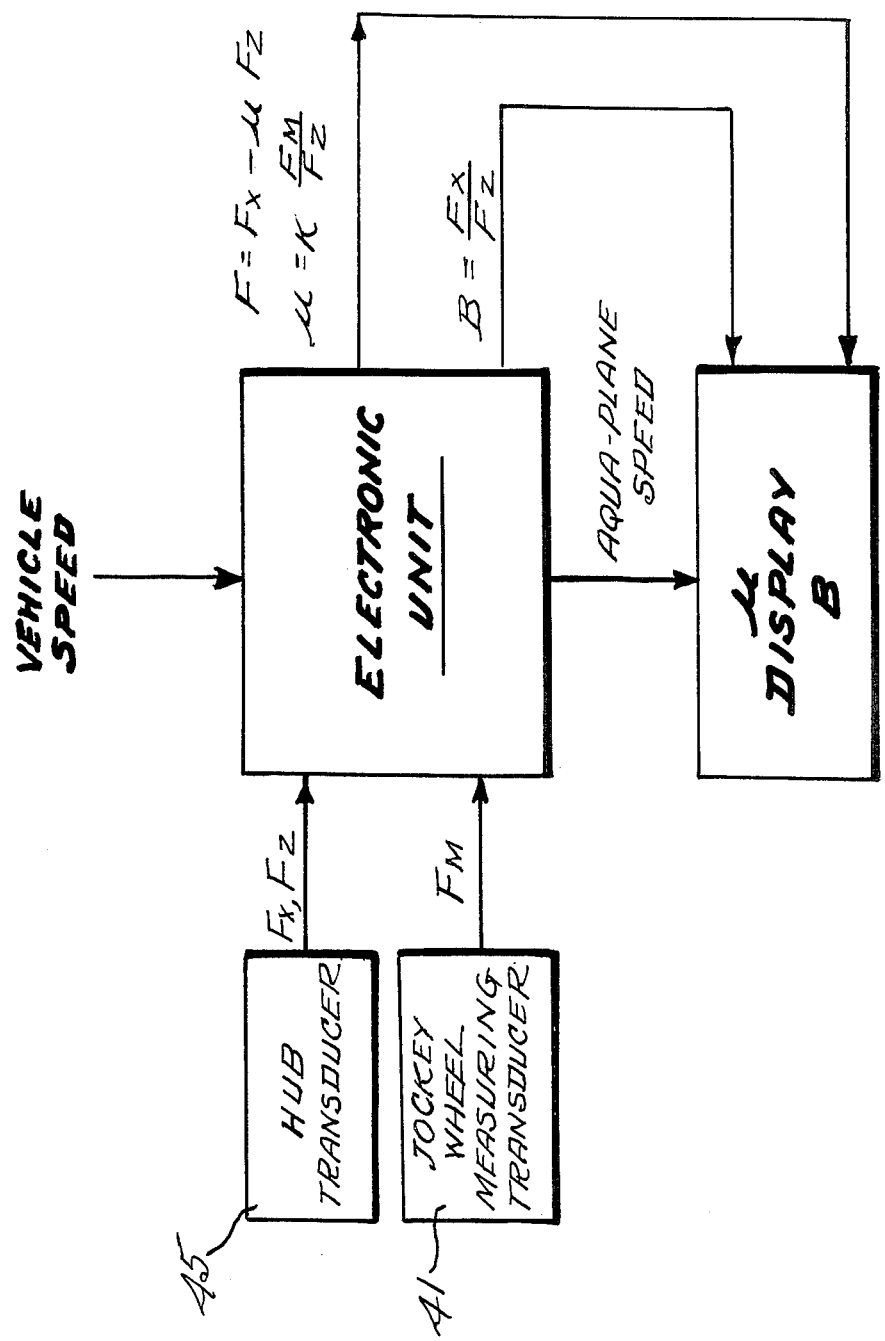

Further features distinguishing the invention are apparent from the following claims and can also be read from the following description of an embodiment exemplifying the invention. The description is referring to the appended drawings on which FIG. 1 shows a schematical sideview of a measuring wheel arrangement according to the invention, installed in the rear of an automobile, FIG. 2 shows the same measuring wheel arrangement in a longitudinal section, FIG. 3 shows in a sideview to an enlarged scale and partly in section, portions of the measuring wheel arrangement according to FIG. 1, and FIG. 4 shows a block diagram of the electronic components.

Figure 2:
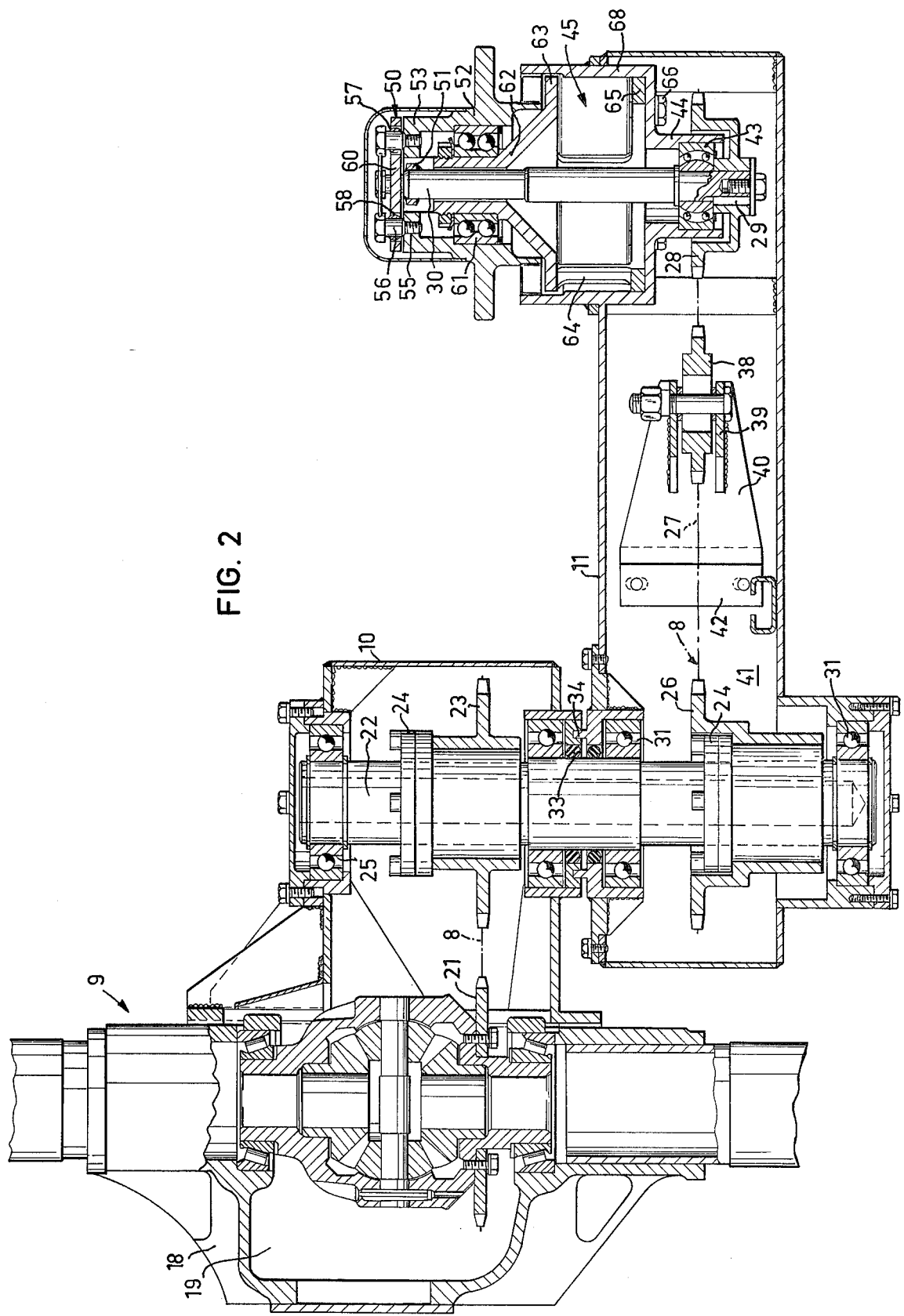

In the embodiment of the measuring wheel arrangement according to the invention, exemplified in FIG. 1, a measuring wheel 3 is built into an automobile 2 and placed half-way between the rear wheels 4 of the automobile 2. The measuring wheel 3 is in driving force transmitting communication with the rear wheels 4 of the automobile by means of a chain transmission 8 and a rear axle transmission 9 conventional for rear-wheel-drive vehicles. The chain transmission 8 is divided into two gears each built into separate housings 10 and 11. The inner housing 10 is rigidly connected to the rear axle chassis member 18 extending between both the rear wheels 4 of the vehicle. Parallel to the rear member 18, a lay shaft 22 is journalled for rotation in the other end of the inner housing 10, and at one outer side of the housing 10 the housing 11 is pivotably mounted on the lay shaft 22. Accordingly, this constitutes a communicating link between both housings 10 and 11, whereby the outer housing 11, at the outer end of which the measuring wheel 3 is mounted for rotation, is pivotable in a vertical plane relative to the inner housing 10. In the embodiment exemplified in FIG. 1, the measuring wheel 3 assumes a position ready for measurement. By means of a lifting device 12, operable from the driver's seat, the measuring wheel 3 can be lifted to an upper position by pivoting about the lay shaft 22, this position being illustrated by a chain dotted contour in FIG. 1. The lifting device 12 comprises a hydraulic cylinder 13 attached to the vehicle chassis, which cylinder is attached to the housing 11 via a bell crank and cable 14 for lifting up the measuring wheel 3 to an upper inactive position. No measurement is done in this upper position 15, and the vehicle 2 can be used without paying attention to the measuring apparatus. The power transmitting connection between the rear wheels 4 of the vehicle and the measuring wheel 3 is to advantage disconnected in this position. This can be accomplished by an engageable and disengageable dog clutch (not shown).

The maximum downward pivoting movement of the housing 11 is limited by means of an arm 16, attached to the housing 11, which via a cable 17 is connected to the supporting portions of the vehicle chassis, for the cases where the vehicle 2 is driven on a very uneven substructure. Cables are used because cables do not constitute sources of disturbance during measurement, since they have small weight and are slack when the measuring wheel 3 assumes a normal measuring attitude to the substructure.

In its lower position the measuring wheel is acted on by a vertical load from a weight arm 5 having a weight mounted in its outer end. The weight arm 5 is pivotably supported in a rigid part of the automobile 2, so that the weight arm 5 can make compensating vertical oscillations in response to the swinging movements of the automobile 2. The force from the weight arm 5 is transferred to the measuring wheel 3 via a helical spring 6 enclosing a cylindrical shock absorber 7.

The rear axle member 18 of the vehicle 2 comprises the rear axle transmission 9 with two driving shafts (not shown) and a differential 19 (FIG. 2). Generally parallel with the member 18 and the lay shaft 22 there extends a strut 20 which is attached at one end to the member 18 and at the other to supporting portions of the vehicle chassis. The strut 20 has the task of taking up sideways forces possibly acting on the rear axle member 18.

The differential 19 is connected to the two rear wheels 4 of the vehicle 2 by means of two driving shafts (not shown). The conventional crown wheel of the differential 19 is exchanged in the exemplified measuring automobile by a first chain wheel 21 which via a chain (not shown) is in power transmitting communication with a second chain wheel 23 attached to the lay shaft 22. The chain wheel 23 is attached to the lay shaft 22 by means of an expandable bushing 24 which is known per se. The lay shaft 22 is by means of rolling bearing 25 journalled for rotation in the housing 10, which is arranged to enclose the differential 19 and the to contain the necessary lubricant for it and the chain gear. Outside the housing 10 the lay shaft 22 carries a third chain wheel 26 which in the same way as the second chain wheel 23 is non-rotatably attached to the lay shaft 22. It will be seen from FIG. 3 how the third chain wheel 26 coacts via a chain 27 with a fourth chain wheel 28 which by means of a key joint 29 is rigidly attached to a drive shaft 30 non-rotatably attached to the measuring wheel 3. Both the third and fourth chain wheels 26, 28 are enclosed in the housing 11 which is pivotably mounted on the lay shaft 22 by means of rolling bearings 31. Also the housing 11 contains lubricant which can be changed by removing a plug 32 in at least one opening made in the rear end of the housing. The passage of the lay shaft 22 through the adjacent housing walls 10, 11 is suitably sealed by sealing rings 33 engaging the lay shaft 22 and an outer labyrinth sealing 34.

The chain 27 shown in FIG. 3 is kept comparatively slack along its upper part between the chain wheels 26 and 28, but it is kept under a certain amount of tension by means of a jockey wheel 36, adjustable in height. During a measuring cycle, the lower part 37 of the chain 27 is kept tensioned as a result of the chain wheel 28 on the measuring wheel driving shaft 30 transferring power to the chain wheel 26 on the lay shaft 22 via the lower part 37 of the chain 27. The transmission gearing is namely so selected that the measuring wheel 3 has a certain reduced rotational speed which is about 15% under the wheel rotational speed corresponding to free rolling. The measuring wheel 3 therefore slips against the substructure during measurement and thus attempts to rotate more rapidly than it is allowed to do. This tendency to increase rotational speed of the measuring wheel 3 results in transmission of driving torque from the measuring wheel 3 to the rear wheels 4 of the vehicle 2.

Since the driving torque transmission to the rear wheels 4 thus compensates to a certain extent the braking force exerted by the measuring wheel 3 on the vehicle 2, measurement with the apparatus according to the present invention is not so demanding of power from the prime mover as is the case with friction measuring devices working only with braked measuring wheels. The rapid accelerations required for measuring on airfields can thus, with the apparatus according to the present invention, be accomplished by an automobile with comparatively small engine power.

The driving torque on the measuring wheel 3 is measured by measuring the chain force acting on the radius of the fourth chain wheel 28, said radius thereby serving as a moment arm. The tensional force in the chain 22 is measured by pressing a jockey wheel 38 against the lower part 37 of the chain. The jockey wheel 38 is rotatably mounted in a bearing bracket 39 welded to one end of a supporting arm 40, the other end of which is rigidly connected with a projecting bracket 42 which is attached to the inner of the lower wall 41 of the housing 11. The upper and lower sides of the supporting arm 40 are provided with strain gauges comprising a wheel measuring transducer 41 (FIG. 4) which provides in a known way by means of an electric circuit information as to the deflection of the supporting arm 40. Such deflection represents the force acting on the jockey wheel 38, which is proportional to the force in the chain and thereby to the driving torque.

The driving shaft 30 attached to the measuring wheel 3 is journalled at one end by means of a spherical ball-bearing 43 in a cylindrical housing 44 rigidly connected to the housing 11. The housing 44 houses a measuring transducer 45, from now on called "hub transducer", which detects forces acting on the measuring wheel 3.

The other, outer end of the drive shaft 30 is provided with a welded-on arm 51, which is a part of an articulated connecting means 50 between the drive shaft 30 and a hub 52 carrying the measuring wheel. The connecting means 50 can be compared with a universal joint where ingoing and outgoing forces act from the same direction. The two knuckles of the universal joint correspond in the present structure to the welded-on arm 51 and the outer end 53 of the hub 52, said outer end having across the central axis a through-going recess in which the drive shaft arm 51 is accommodated with play. Both the arm 51 and the hub end 53 are provided with threaded holes 55 for attaching a number of pins 56 having spherical outer bearing surfaces 57 in a number of holes provided with bearing bushes 58 in a circular plate 60 corresponding in its function to the cross-piece in a normal universal joint.

Because of the articulated connecting means 50 and the mounting in the spherical ballbearing 43 a certain amount of misalignment of the drive shaft 30 is possible, which ensures that during measurement the drive shaft 30 will not affect the transfer of force between the hub 52 carrying the measuring wheel 3 and the hub transducer 45. Via a rolling bearing 61, placed symmetrically from the point of view of wheel loading, the hub 52 is rotatably mounted on an outwardly directed neck-portion 62 of the hub transducer 45. This further comprises an outer ring 63 made integral with said neck portion. The outer ring 63 is connected to an inner ring 65 via four rods 64, parallel to the drive shaft, said inner ring 65 being fastened to the bottom of an outwardly open barrel 68 in the cylindrical housing 44. There is free play between the barrel 68 and the outer ring 63. The neck portion of the hub transducer 45 has sufficient play with reference to the drive shaft 30 running through it that misalignment of the shaft can take place without measurement of the force applied to the wheel 3 being disturbed. The hub transducer 45, equipped with rods 64, is known per se, and therefore its function will only be described summarily. The rods 64 are rigidly secured to the rings 63 and 65. When the measuring wheel is loaded the rings 63 and 65 are displaced in relation to each other, whereby the rods 64 are deformed and assume an S-like shape. The cross-section of the rods 64 is substantially quadratic and by means of strain gauges (not shown) attached to the sides of the rods, loads on the measuring wheel 3 can be sensed. By placing the strain gauges at least on adjacent sides on each rod, detection of both vertical and horizontal loads on the measuring wheel 3 is possible. The horizontal load is thereby an expression for the total braking force which the measuring wheel 3 transfers to the vehicle 2. The total braking force constitutes the sum of the frictional force with which the wheel is affected on contact with the substructure, and the roll resistance, which is the horizontal force which primarily comes from the work done by the wheel in pushing away snow, water or the like lying on the substructure. The braking effect of a wheel is often expressed by the term braking force number, which is obtained when the total braking force is put in relation to the wheel load.

Accordingly, by means of the described measuring apparatus, the coefficient of friction $\mu$ can be indicated in the measuring equipment by the load $F_Z$ being measured with the hub transducer 45, and the tensional force $F_M$ in the chain 27 being measured with the jockey wheel measuring transducer 41, whereafter $F_M$ is divided by $F_Z$ in a conventional electronic unit installed in the vehicle 2. The quotient thus obtained is multiplied by a constant factor K corresponding to the quotient between the radii of the chain wheel 28 and measuring wheel 3. A product is thereby obtained which represents the coefficient of friction $\mu$.

The hub transducer 45 also enables the braking force number B for the substructure in question to be calculated. This is done by measuring the total braking force $F_X$ coming from the measuring wheel 3 by the hub transducer 45, whereafter $F_X$ is divided by the normal load $F_Z$ in the electronic unit to give the braking force number B.

Supplementary to the braking force number there is also produced a measure of the roll resistance of the course. The friction force F, constituting the product of the coefficient of friction $\mu$ and the load $F_Z$, is thereby subtracted from the total braking force represented by the $F_X$ signal. In this connection, the friction force can optionally be represented by the signal $F_M$ representing the force in the chain.

All the necessary instruments and operating means for carrying out the measurements are collected in the driver's cockpit.

In measuring the coefficient of friction $\mu$ on a dry course substantially the following measures are carried out. By operating a control intended for the purpose the measuring wheel 3 is lowered to its position engaging against the course. The electronic unit for processing measuring signals is switched on and a push button for measuring the coefficient of friction is depressed. The course length which is to be travelled as a measuring distance is set on the panel with a thumbwheel switch. The vehicle is accelerated up to the intended measuring speed and when measuring is to begin a starting button is pressed. Thereby the jockey pulley transducer 41 and the hub transducer 45 begin to transmit signals representing $F_M$ and $F_Z$ respectively. As mentioned hereinbefore, these signals are converted electrically in the electronic unit to an output representing the coefficient of friction $\mu$ and a signal representing the average value of $\mu$ over the distance travelled. These signals are indicated on a displaying instrument and are also registered on a recorder if so desired. The average value of $\mu$ can also be indicated in digital form on a display unit upon termination of measurement. For measuring of coefficient of friction $\mu$ on a dry course, the signal representing $F_X$ can be used instead of the $F_M$ signal, whereby the electronic unit analogous with the signal processing in forming the braking force number gives an output signal which closely agrees with the friction conditions of the substructure.

In measuring on a rain-soaked course, especially for airfields, it is important to be able to estimate at which speed aquaplanning occurs. Aquaplanning is said to be in the offing when the coefficient of friction assumes values between 0.25 and 0.15. After the preparatory measures set forth above for putting the measuring apparatus in order for measuring, the vehicle is accelerated up to the speed where $\mu$ obtains the value 0.20, whereafter the speed over the whole of the measuring course is regulated by the driver so that the $\mu$ value lies within the range of 0.15 to 0.25, all the time. The speed can naturally be noted manually by the driver, but in a more developed version of the electronic signal processing, the notations are made automatically by the electronic unit. This can comprise a micro computer which can store the speed registrations and further calculate an average speed for aquaplanning over the measuring course travelled. For achieving such a calculation in the micro computer a special press button for water aquaplanning measurement can be depressed before starting measurement. On termination of measurement the average value calculated for the aquaplanning speed is fed out onto a display unit after pressing a button for the result output. The aquaplanning speed can also be registered on a recorder if so desired.

In measuring on a course, e.g. a runway, covered with snow, slush and/or collections of water, it is important to be able to measure the roll resistance for a vehicle, since roll resistance on such a substructure affects vehicle braking to a large degree. Apart from obtaining information as to at which speed one can count on aquaplanning it is therefore also of value for an aeroplane to obtain information on how great the total braking effect is which can be obtained on the substructure in question. For such measurement the measuring device is prepared in the same way as mentioned previously and in this case a button is also pressed for braking force number measurement.

The hub transducer 45 hereby applies a signal to the electronic unit representing the total braking force $F_x$, which is divided in the electronic unit by the input signal representing the normal loading $F_z$, to form a signal value corresponding to the braking force number. This is registered on a recorder in the instrumental equipment but can also be fed out as an average value for the whole measuring course onto a display unit after pressing the result fee-out-button. In a corresponding way as for the braking force number, the measuring apparatus can be adapted for measuring and producing a separate value for roll resistance.

The values indicated on the instruments in the vehicle for coefficient of friction, aquaplanning speed, roll resistance and braking force number are all obtained from the coaction of the measuring wheel with the substructure. The measuring wheel is of standardized type and its coaction with the substructure depends on the type of tire selected and naturally differs from the behavior of the other tire types. When using the measuring apparatus according to the invention for airfields, the measuring values obtained must therefore be corrected with regard to the differences in the tires in question before the pilot in an aeroplane is informed on the limiting values applying to the aeroplane relating to take-off or landing speed as well as relevant data for decelerating the aeroplane.

According to the exemplified embodiment, the measuring apparatus according to the invention is preferably built into an automobile, the electronic unit incorporated in the measuring equipment being placed in the boot of the vehicle or in some other out-of-the-way place while the instruments connected to the electronic unit can be integrated into the vehicle dashboard or the like. In the forward portion of the automobile, and easily accessible from the driver's seat, there are also placed the controls for the measuring apparatus and when more advanced indications of the measuring values are needed, further registrating apparatuses can be arranged within sight and reach of the dirver's seat.

Such installation of measuring apparatus and measuring equipment will enable a measurement to be started and carried out very quickly, where the values for all the parameters of importance for driving and braking vehicles on a prevailing substructure can be determined. Since the measuring wheel can be caused in a simple way to assume an upper inactive position under the automobile, an automobile equipped in this way can also be used as a passenger automobile in a conventional manner.

The invention is not limited to the embodiment example described hereinbefore but within the framework of the inventive idea and the following claims it can be modified into a variety of embodiments. It is thus obvious that the constructional solutions for the transmission, raising device etc. only constitute descriptive examples and corresponding practical solutions can be varied in many different ways.

We claim:

1. A method of measuring and indicating limiting values for driving and braking vehicles on a substructure comprising the steps of:

bringing a measuring wheel mounted on a vehicle engage said substructure with a predetermined slip in relation to vehicle speed, measuring the loads acting on said measuring wheel to produce measuring signals, combining said measuring signals in an electronic unit to produce signals indicating said limiting values, and producing a display of said limiting values.

2. A method of measuring as in claim 1 wherein said step of combining includes dividing a signal representing the momentary horizontal load on the measuring wheel by a signal representing the momentary vertical load to produce a signal indicating braking force number.

3. A method of measuring as in claim 1 wherein said step of combining includes dividing a signal representing momentary torque on the measuring wheel by a signal representing momentary vertical load to produce a signal indicating the coefficient of friction.

4. A method of measuring as in claim 3 wherein said step of combining includes forming a signal representing the product of the coefficient of friction and the momentary wheel load and subtracting that product signal from a signal representing the horizontal wheel load produce a signal indicating resistance to rolling.

5. A method as in claim 3 wherein said step of combining includes forming a signal proportional to the torque acting on the measuring wheel and subtracting the torque signal from a signal representing the horizontal wheel load to produce a signal indicating resistance to rolling.

6. A method as in claim 1, wherein said step of bringing includes the step of bringing said wheel to engage so that said wheel rotates in a plane parallel to the direction of the direction of vehicle movement.

7. An apparatus for measuring and indicating limiting values for driving and braking vehicles on a substructure, comprising a measuring wheel, means for pivotally mounting said wheel in a wheeled vehicle so as to be raisable and lowerable to engage and disengage said substructure means for transmitting torque to said wheel with a predetermined reduction gearing from at least one of the ordinary wheels of the wheeled vehicle, at least one measuring transducer, means for mounting said transducer at the measuring wheel for scanning loads acting on the measuring wheel to produce measuring signals corresponding to the loads, and an electronic unit for processing said measuring signals to produce signals indicating said limiting values.

8. Apparatus as claimed in claim 7, wherein said wheel mounting means includes an arm and an arm housing and the measuring transducer includes two rings and a number of rods fastened between said rings with one ring formed on the outside with a neck portion carrying the measuring wheel for rotatable journalling and the second ring rigidly connected to the outer end of said arm housing.

9. Apparatus as claimed in claim 8, wherein said transmitting means includes a bearing housing and a driving shaft mounted in said bearing housing for rotatable and sideways tip-able movement, said shaft being connected to an outer end of the arm housing so that the drive shaft passes freely through the measuring transducer and so articulately connected to the measuring wheel that the drive shaft can be put out of alignment relative to the measuring wheel and/or arm housing.

10. Apparatus as claimed in claim 7, further including at least one measuring transducer for scanning torque acting on the measuring wheel and wherein said transmitting means comprises at least one chain transmission with a chain and a chain housing, the measuring transducer scanning the torque to sense the force in the chain transmission, said force being directly proportional to the torque acting on the measuring wheel.

11. Apparatus as claimed in claim 10, wherein said the torque-scanning measuring transducer includes a jockey pulley engaging against the chain, said pulley being rotatably journalled at an outer free end of an arm, the opposite end of which is rigidly fixed in said chain housing.

12. Apparatus as claimed in claim 10, wherein said the electronic unit receives input signals from the measuring transducers and includes means to feed out signals to instruments connected to it for display of the measuring results.

13. Apparatus as claimed in claim 7, wherein said transmission means comprises a conventional rear axle transmission for the rear wheels of the automobile, having two driving shafts and a differential and a crown wheel in the differential shaped as a chain wheel incorporated in the chain transmission.

14. Apparatus as claimed in claim 13, wherein the chain transmission including of two series-connected chain gears incorporated in separate housings a first chain housing being rigidly attached to a housing surrounding the differential and that a second chain housing being pivotably mounted at one end in the first chain housing to carry the measuring wheel at its other end.

15. Apparatus as claimed in claim 14, wherein said measuring wheel mounting means includes a hydraulic lifting device operable from the driver's cockpit in the automobile.

16. Apparatus as in claim 7, wherein said mounting means mounts said wheel for rotation in a plane parallel to the direction of vehicle movement.

* * * * *